US005723617A

United States Patent [19]

Cuny

[11] Patent Number: 5,723,617
[45] Date of Patent: Mar. 3, 1998

[54] PYRROLO[2,1-A]ISOQUINOLINE DYES

[75] Inventor: Gregory D. Cuny, Woodbury, Minn.

[73] Assignee: Minnesota Mining and Manufacturing Company, Saint Paul, Minn.

[21] Appl. No.: 576,502

[22] Filed: Dec. 21, 1995

[51] Int. Cl.[6] ............................................. C07D 221/06
[52] U.S. Cl. .......................... 546/94; 430/219; 430/517; 430/551; 430/598; 430/613
[58] Field of Search .......................... 546/94; 430/219, 430/517, 551, 598, 613

[56] References Cited

U.S. PATENT DOCUMENTS

| | | | |
|---|---|---|---|
| 3,260,601 | 7/1966 | Bailey | 96/84 |
| 3,398,145 | 8/1968 | Bailey | 260/240.4 |
| 3,573,057 | 3/1971 | Stevens | 96/112 |
| 4,147,554 | 4/1979 | Tanaka et al. | 96/130 |
| 4,599,300 | 7/1986 | Tanaka et al. | 430/411 |
| 5,196,393 | 3/1993 | Kubodera et al. | 503/227 |

FOREIGN PATENT DOCUMENTS

| | | |
|---|---|---|
| 60-121440 | 6/1985 | Japan. |
| 1-049684 | 2/1989 | Japan. |
| 1-049685 | 2/1989 | Japan. |
| 2-062280 | 3/1990 | Japan. |
| 5-124337 | 5/1993 | Japan. |

OTHER PUBLICATIONS

J. Fabian, "Near-Infrared Absorbing Dyes", *Chem. Rev.*, 92, 1992, pp. 1197-1226.

C.K. Bradsher and R.W.L. Kimber, *J. Org. Chem.*, 30, 1965, pp. 1846-1849.

C. Casagrande et al., "Synthesis and Pharmacological Evaluation of Some Pyrrolo[2,1-a]isoquinolines", *J. Med. Chem.*, 11, 1968, pp. 765-770.

M. Iwao and T.. Kuraishi, *Bull. Chem. Soc. Jap.*, 53, 1980, pp. 297-298.

A. Buzas et al., *Heterocycles*, 23, 1985, pp. 2561-2570.

*Primary Examiner*—Alan L. Rotman
*Assistant Examiner*—Evelyn Huang
*Attorney, Agent, or Firm*—Walter N. Kirn; Gregory A. Evearitt; Arlene K. Musser

[57] ABSTRACT

A series of novel pyrrolo[2,1-a]isoquinoline dyes has been prepared using readily available starting materials via a simple synthetic pathway. These dyes have narrow absorption bands in the range of 500-900 nm. Those that absorb in the near-infrared region (700-1400 nm) lack significant absorption in the 300-400 nm ultraviolet region of the spectrum; this is an advantage for use in an applications such as imaging setting film. In addition, the greater thermal and chemical stability of these dyes in comparison to their indolizine analogues should be valuable in many applications.

16 Claims, No Drawings

PYRROLO[2,1-A]ISOQUINOLINE DYES

FIELD OF INVENTION

This invention relates to novel dyes having narrow absorption bands in the visible or near-infrared region of the spectrum. These dyes are useful in applications requiring dyes to suppress halation or to convert light-to-heat.

BACKGROUND

Single-mode laser diodes and diode-pumped lasers, both emitting radiation in the near-infrared region of the electromagnetic spectrum, are now commercially available. These laser sources have made possible the development of compact, efficient, and relatively inexpensive recording devices. Rapid growth in a broad range of fields, including optical recording, thermal writing displays, laser printers, laser filters and infrared photography, has resulted. This growth has created a demand for media that contains near-infrared absorbing materials to support these technologies.

It is well known that black body absorbers can be used to absorb near-infrared radiation. These highly colored absorbers include both dyes and pigments (e.g., carbon black) that absorb strongly throughout the visible and near-infrared spectrum. Although such highly colored materials have been used in black and white imaging systems, their use is often prohibited in color imaging systems that require color purity in the resulting image; the highly colored absorber frequently contaminates the colored image. Dyes that strongly absorb in the near-infrared without significantly absorbing in the visible spectrum are currently the best choice for maintaining color purity in color imaging systems.

Although a variety of near-infrared absorbing dyes is known in the literature, most of these dyes are not commercially available due to lack of readily available starting materials, lack of simple synthetic pathways, or lack of both. Often a suitable dye for an application is either not available or prohibitively expensive; this precludes development of the application. For example, near-infrared absorbing dyes having narrow absorption bands are often sought for uses such as suppression of halation in infrared film and conversion of light-to-heat in laser imaging systems. These uses require an infrared dye lacking visible absorption to maintain color purity in the resulting image. The lack of commercially available dyes meeting these requirements has limited the development of these technologies.

There is a need for new dyes having narrow absorption bands in the near-infrared that can be prepared by simple synthetic pathways from readily available starting materials.

SUMMARY

A series of novel pyrrolo[2,1-a]isoquinoline dyes has been prepared using readily available starting materials via a simple synthetic pathway. These dyes have narrow absorption bands in the range of 500–900 nm. Those that absorb in the near-infrared region (700–1400 nm) lack significant absorption in the 300–400 nm ultraviolet region of the spectrum. This is an advantage for use in applications such as imaging setting film. In addition, the greater thermal and chemical stability of these dyes in comparison to their indolizine analogues should be valuable in many applications; cyanine dyes containing the pyrrolo[2,1-a]isoquinoline moiety have shorter bridging units than indolizine dye analogues with comparable absorption maxima, and shorter bridging units are known to result in increased stability for cyanine dyes.

Dyes of the present invention have a central pyrrolo[2,1-a]isoquinoline nucleus of the formula:

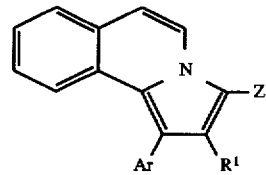

wherein Ar is a phenyl group; $R^1$ is an alkyl, alkaryl, aralkyl or aryl group; and Z represents the group of atoms that includes either a positively charged nitrogen atom ($N^+$), a carbonyl group (C=O), or a nitrile group (CN) and completes a conjugate chain between the nitrogen atom of the pyrrolo[2,1-a]isoquinoline nucleus and the positively charged nitrogen atom, carbonyl group, or nitrile group contained in Z. Conjugate means that the substituent is capable of delocalized bonding between the positively charged nitrogen, carbonyl group or nitrile group within the substituent and the nitrogen of the pyrrolo[2,1-a]isoquinoline nucleus.

In one embodiment, dyes of the present invention have a central nucleus of the formula:

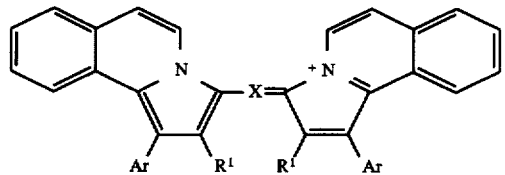

I wherein Ar is a phenyl group; $R^1$ is an alkyl, alkaryl, aralkyl or aryl group; and X is selected from the bridging groups consisting of:

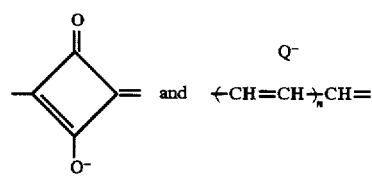

wherein n is 0, 1 or 2 and $Q^-$ is an anion.

In still another embodiment, dyes of the present invention have a central nucleus of the formula:

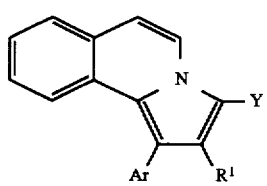

II wherein Ar is a phenyl or substituted phenyl group; $R^1$ is an alkyl, alkaryl, aralkyl or aryl group; and Y is selected from the group consisting of:

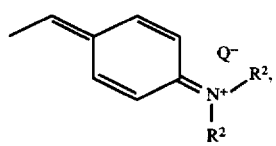

-continued

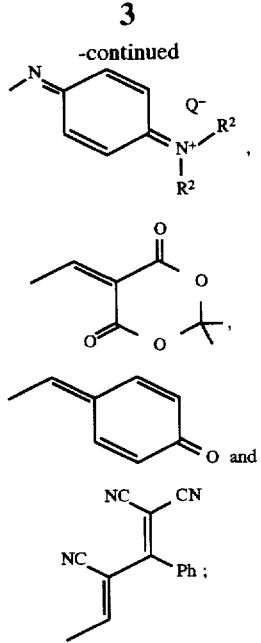

wherein each $R^2$ is independently an alkyl group having from 1 to 8 carbon atoms and $Q^-$ is an anion.

When the term "group" is used in defining a chemical species or component, it is understood that placing conventional substituents on that group is contemplated by the invention. For example, the term "alkyl group" covers not only unsubstituted alkyl such as methyl, ethyl, hexyl, cyclohexyl, isooctyl and the like, but also includes hydroxyethyl, omega-chlorohexyl, 2-ethoxy-dodecyl and the like. When the term "alkyl" or "alkyl moiety" is used, no substitution is included within the use of that term. Similarly, when a general structure is referred to as a compound having the "central nucleus" of a given formula, any substitution which alters neither the bond structure of the formula nor the shown atoms within that structure is included. For example, where a polymethine chain is shown between two defined heterocyclic nuclei, the chain may be rigidized by a cyclic group, and substituent groups may be placed on the chain, but the conjugation of the chain may not be altered, and the atoms shown in the heterocyclic nuclei may not be replaced. The description of a formula as a "general formula" does not specifically allow for such broader substitution on the structure.

Other aspects, advantages, and benefits of the present invention are apparent from the detailed description, the examples and the claims.

DETAILED DESCRIPTION OF INVENTION

A class of dyes of the present invention has a central nucleus of the formula:

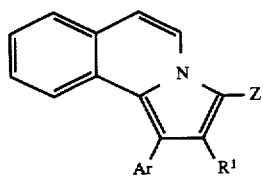

wherein Z is selected from the group consisting of

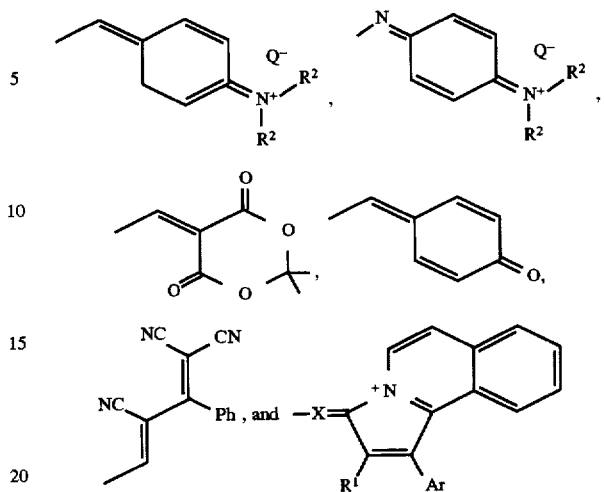

wherein Ar is a phenyl or substituted phenyl group; $R^1$ is an alkyl, alkaryl, aralkyl or aryl group; each $R^2$ is independently an alkyl group having from 1 to 8 carbon atoms; $Q^-$ is an anion, preferably one selected from the group consisting of $Cl^-$, $Br^-$, $I^-$, $F^-$, $ClO_4^-$, $PF_6^-$, $HSO_4^-$, $HCO_3^-$, $SbF_6^-$, $AsF_6^-$, $R_fSO_3^-$, $(R_fSO_2)_3C^-$, $(R_fSO_2)_2HC^-$, and $(R_fSO_2)_2N^-$ wherein $R_f$ represents a perfluoroalkyl group or two $R_f$ groups taken together represent the necessary atoms to form a five- or six-membered perfluorinated ring; and X is selected from the bridging groups consisting of:

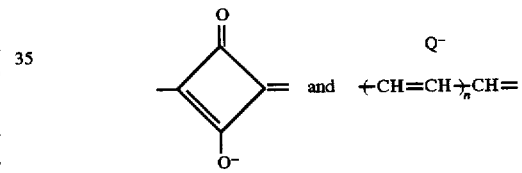

wherein n is 0, 1 or 2 and $Q^-$ is as defined above.

In one embodiment, dyes of the present invention have a central nucleus of the formula:

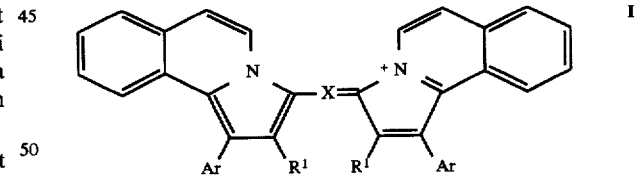

wherein Ar is a phenyl or substituted phenyl group; $R^1$ is an alkyl, alkaryl, aralkyl or aryl group and X is selected from the bridging group consisting of:

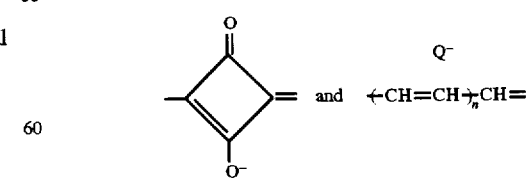

wherein n is 0, 1 or 2 and $Q^-$ is an anion, preferably one selected from the group consisting of $Cl^-$, $Br^-$, $I^-$, $F^-$, $ClO_4^-$, $PF_6^-$, $HSO_4^-$, $HCO_3^-$, $SbF_6^-$, $AsF_6^-$, $R_fSO_3^-$, $(R_fSO_2)_3C^-$, $(R_fSO_2)_2HC^-$, and $(R_fSO_2)_2N^-$ wherein $R_f$ represents a perfluoroalkyl group or two R$_f$ groups taken together represent the necessary atoms to form a five- or six-membered perfluorinated ring.

Preferred dyes having a nucleus of Formula I include those having the formula:

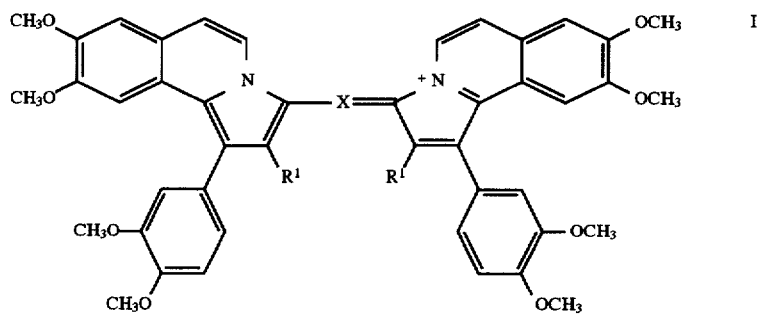

wherein X is as defined above and R$^1$ is methyl or phenyl.

In another embodiment, dyes of the present invention have a central nucleus of the formula:

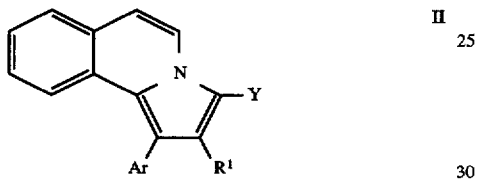

wherein Ar is a phenyl or substituted phenyl group; R$^1$ is an alkyl, alkaryl, aralkyl or aryl group; and Y is selected from the group consisting of:

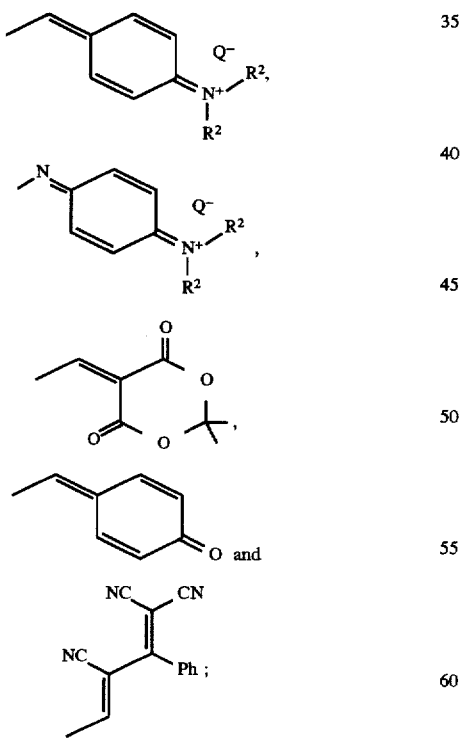

wherein each R$^2$ is independently an alkyl group having from 1 to 8 carbon atoms and Q$^-$ is an anion, preferably one selected from the group consisting of Cl$^-$, Br$^-$, I$^-$, F$^-$, ClO$_4^-$, PF$_6^-$, HSO$_4^-$, HCO$_3^-$, SbF$_6^-$, AsF$_6^-$, R$_f$SO$_3^-$, (R$_f$SO$_2$)$_3$C$^-$, (R$_f$SO$_2$)$_2$HC$^-$, and (R$_f$SO$_2$)$_2$N$^-$ wherein R$_f$ represents a perfluoroalkyl group or two R$_f$ groups taken together represent the necessary atoms to form a five- or six-membered perfluorinated ring.

Preferred dyes having a nucleus of Formula II include those having the formula:

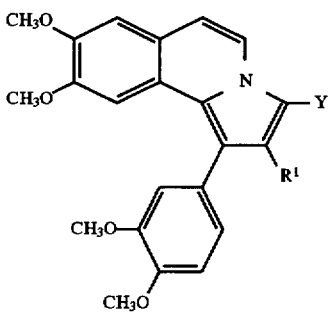

wherein Y is as defined above and R$^1$ is methyl or phenyl.

A series of novel pyrrolo[2,1-a]isoquinoline dyes was prepared from readily available starting materials via a simple synthetic pathway. One such starting material is papaverine, a naturally occurring alkaloid that is relatively inexpensive and commercially available as its hydrochloride salt. Papaverine hydrochloride was converted to its free base in 97% yield. The free base was subsequently alkylated with phenacyl bromide in refluxing acetone to give 1 in 56% yield (Scheme 1). Refluxing the mixture for one hour produced good results; additional heating resulted in substantial decomposition of 1 to papaverine hydrobromide. Attempts to isolate 1 using benzene as solvent were unsuccessful. Sodium bicarbonate in water was mixed with 1 to give the cyclized product 2 in 82% yield.

Scheme 1

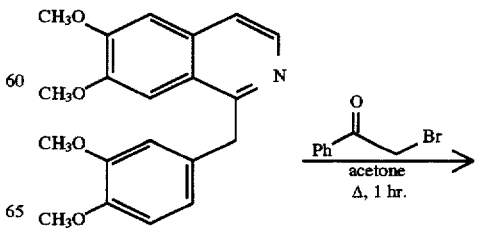

-continued
Scheme 1

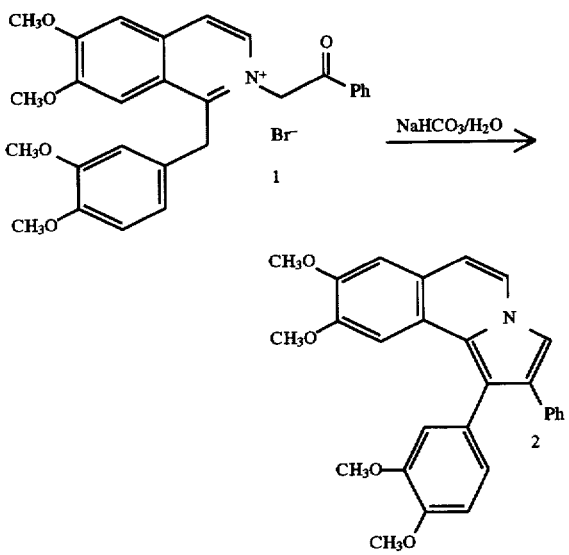

Similarly, 8,9-dimethoxy-1-(3,4-dimethoxy)phenyl-2-methylpyrrolo[2,1-a]isoquinoline was prepared from papaverine and iodoacetone that had been generated in situ from chloroacetone and sodium iodide via a Finkelstein reaction.

Dyes having a nucleus of Formula I were prepared by reacting two molar equivalents of pyrrolo[2,1-a]isoquinoline derivatives with one molar equivalent of various bridging units. For example, the pyrrolo[2,1-a]isoquinoline derivative 2 was converted into squarylium innersalt dye 3 by allowing 2 to react with squaric acid (0.5 eq.) in butanol/toluene (1:1) at reflux for 3 hrs. Similarly, N-[5-(phenylamino)-2,4-pentadienylidene]aniline monochloride (0.5 eq.) was allowed to react with 2 (1 eq.) in the presence of perchloric acid (HClO$_4$, 1 eq.) and triethylamine (1.2 eq.) in acetic anhydride to give dye 4. Dyes 5 and 6 were prepared in a similar manner utilizing triethylorthoformate and malonaldehyde bis(dimethyl acetal), respectively, as the bridging group precursors. Dye 13 was prepared by allowing 8,9-dimethoxy-1-(3,4-dimethoxy)phenyl-2-methylpyrrolo[2,1-a]isoquinoline (1 eq.) to react with 0.5 eq. malonaldehyde bis(dimethyl acetal) in the presence of perchloric acid (1 eq.) and triethylamine (1.2 eq.) in acetic anhydride.

Dyes having a nucleus of Formula II were prepared by allowing one molar equivalent of pyrrolo[2,1-a]isoquinoline derivatives to react with one molar equivalent of various electrophilic or nucleophilic end groups. For example, dye 7 was prepared by allowing 2 (1 eq.) to react with p-N,N-dimethylaminobenzaldehyde (1 eq.) and perchloric acid (1 eq.) in acetic anhydride. Dye 8 was prepared by allowing 2 (1 eq.) to react with N,N-dimethyl-p-nitrosoaniline (1 eq.) and perchloric acid (1 eq.) in refluxing ethanol. Dye 9 was prepared in an analogous fashion using p-hydroxybenzaldehyde. Dyes 12 and 14 were prepared by allowing pyrrolo[2,1-a]isoquinoline derivatives to react with 5-methoxymethylene-1,3-dioxan-4,6-dione in refluxing ethanol. Using an alternate synthetic strategy, 2 was converted to 8,9-dimethoxy-1-(3,4-dimethoxy)phenyl-2-phenylpyrrolo[2,1-a]isoquinoline-3-carboxaldehyde utilizing phosphorus oxychloride in dimethylformamide (Vilsmeier reaction). The pyrrolo[2,1-a]isoquinoline-3-carboxaldehyde derivative was allowed to react with 3-dicyanomethylene-3-phenylpropionitrile to yield dye 16.

The following non-limiting examples further illustrate the present invention.

EXAMPLES

The materials employed below were obtained from Aldrich Chemical Co. (Milwaukee, Wis.) unless otherwise specified. Papavarine hydrocloride was purchased from Aldrich Chemical Co. Melting points (uncorrected) were recorded using a Thomas melting point apparatus. NMR, spectra were recorded using either a 400 Mz Varian or a 500 Mz Varian Fourier transform spectrometer. Infrared spectra were recorded using a Bomem MB 102 Fourier transform spectrometer. UV/Vis spectra were recorded using a Shimadzu MPC-3100 spectrometer. Molecular weight was determined using an EXTREL FTMS Fourier transform mass spectrometer.

Example 1

This example describes the isolation of the free base papaverine (structure shown below) from the hydrochloride salt:

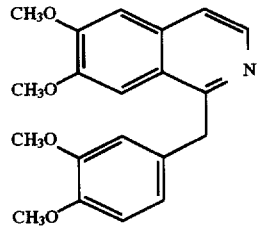

Papaverine hydrochloride (11.3 g, 30 mmol) was dissolved in a mixture of water (150 mL) and ethanol (150 mL). Diethyl ether (150 mL) was added followed by 10% aqueous sodium hydroxide until the aqueous layer was basic. The mixture was extracted twice with chloroform (150 mL each). The organic extracts were combined, washed with brine, dried over anhydrous magnesium sulfate and filtered. The filtrate was concentrated to give a white solid (9.92 g, 97% yield); mp: 146°–148° C.; $^1$H NMR (500 Mz; CDCl$_3$): δ3.77 (s, 3H); 3.81 (s, 3H); 3.90 (s, 3H); 3.99 (s, 3H); 4.53 (s, 2H); 6.76 (d, 1H, J=8.6 Hz); 6.81–6.84 (m, 3H); 7.04 (s, 1H); 7.34 (s, 1H); 7.42 (d, 1H, J=5.6 Hz); 8.37 (d, 1H, J=5.6 Hz).

Example 2

This example describes the preparation of the intermediate 6,7-dimethoxy-1-[(3,4-dimethoxy)benzyl]-N-phenacylisoquinolinium bromide, 1:

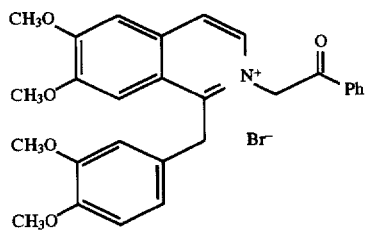

A mixture of papaverine (10.15 g, 30 mmol), phenacyl bromide (6.56 g, 33 mmol) and acetone (100 mL) was heated at reflux for 1 h and then allowed to cool to room temperature. The reaction mixture was poured into diethyl ether (400 mL). The mixture was filtered and the residue was dried to yield 8.98 g of 1 as a pale yellow solid. $^1$H NMR (400 Mz; d$_6$-DMSO): δ3.46 (s, 3H); 3.61 (s, 3H); 3.98 (s, 3H); 4.11 (s, 3H); 5.00 (s, 2H); 6.42–6.46 (m, 1H); 6.60 (s, 2H); 6.69 (d, 1H, J=8.3 Hz); 6.84 (s, 1H); 7.62 (t, 2H, J=8.0 Hz); 7.74–7.82 (m, 2H); 7.92–7.98 (m, 3H); 8.30 (d, 1H, J=6.8 Hz); 8.46 (d, 1H, J=6.8 Hz); IR (KBr): 1692, 1517, 1502, 1235 cm$^{-1}$.

Example 3

This example describes the preparation of the intermediate 8,9-dimethoxy-1-(3,4-dimethoxy)phenyl-2-phenylpyrrolo[2,1-a]isoquinoline, 2:

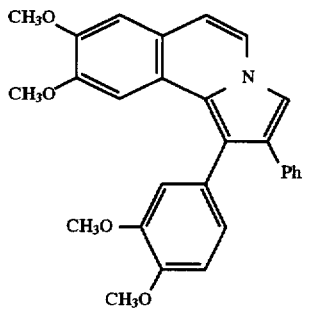

A mixture of 1 (8.50 g, 15.8 mmol), water (650 mL) and sodium bicarbonate (6.82 g) was heated at 55°–60° C. for 2 h. The reaction mixture was allowed to cool to room temperature and then extracted twice with chloroform (400 mL each). The chloroform extracts were combined, washed with water (200 mL) and then brine (100 mL). The chloroform layer was dried using anhydrous magnesium sulfate, filtered and then concentrated to give a pale orange solid. The solid was recrystallized with chloroform/petroleum ether (1:3) to yield 5.70 g of 2 as a tan solid; m.p. 179°–181° C.; $^1$H NMR (500 Mz; CDCl$_3$): δ3.47 (s, 3H); 3.76 (s, 3H); 3.93 (s, 6H); 6.66 (d, 1H, J=7.3 Hz); 6.93–6.96 (m, 2H); 7.00–7.03 (m, 1H); 7.08 (s, 1H); 7.14–7.30 (m, 5H); 7.42 (s, 1H); 7.69 (d, 1H, J=7.3 Hz); $^{13}$C NMR (125 Mz; CDCl$_3$): d 55.19, 55.73, 55.77, 55.87, 100.45, 104.49, 107.78, 110.59, 111.24, 111.76, 114.77, 120.81, 121.65, 122.69, 123.99, 125.79, 126.00, 128.03, 128.24, 129.62, 135.15, 147.60, 147.83, 148.49, 148.90; IR (KBr): 1500, 1474, 1226, 1025, 859 cm$^{-1}$; HRMS: (calc) 439.1778 amu; (found) 439.1770 amu.

Example 4

This example describes the preparation of dye 3:

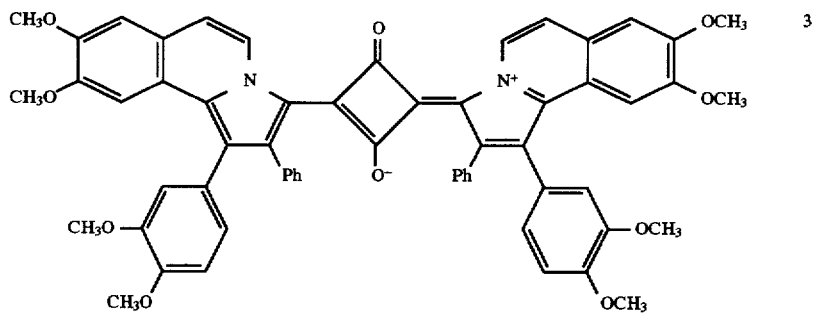

A mixture of 2 (0.878 g, 2 mmol), 3,4-dihydroxy-3-cyclobutene-1,2-dione (0.114 g, 1 mmol), butanol (10 mL) and toluene (10 mL) was heated at reflux for 3 h. The reaction mixture was allowed to cool to room temperature. The mixture was poured into diethyl ether (50 mL) and then filtered. The residue was dried to yield 0.870 g of 3 as a purple solid; $\lambda_{max}$=750 nm(chloroform).

Example 5

This example describes the preparation of dye 4:

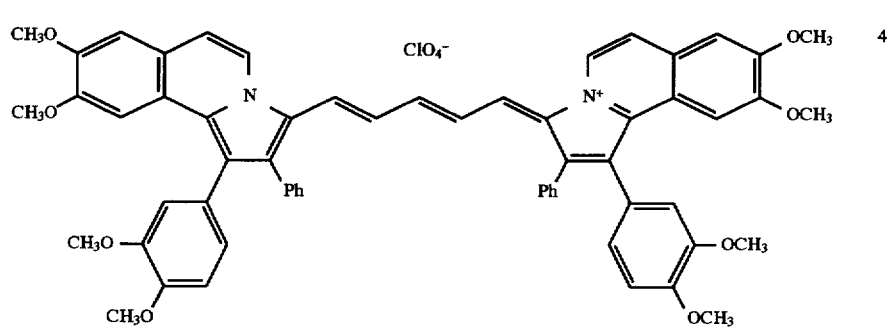

A mixture of 2 (0.439 g, 1 mmol), acetic anhydride (10 mL) and perchloric acid (70%, 0.143 g, 1 mmol) was stirred at room temperature for 5 min. N-[5-(phenylamino)-2,4-pentadienylidene]aniline monochloride (0.142 g, 0.5 mmol) and triethyl amine (0.167 mL, 1.2 mmol) were then added. The reaction was allowed to stud at room temperature for 1 day and then filtered. The residue was washed several times with diethyl ether and dried to yield 0.397 g of 4 as a rest colored crystalline solid; $\lambda_{max}$=871 nm(acetone).

Example 6

This example describes the preparation of dye 5:

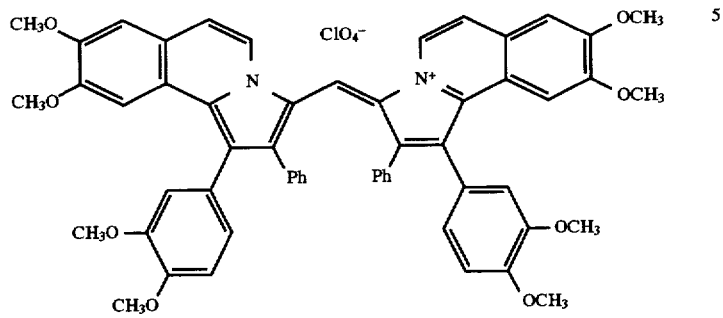

A mixture of 2 (0.439 g, 1 mmol), acetic anhydride (10 mL) and perchloric acid (70%, 0.143 g, 1 mmol) was stirred at room temperature for 5 min. Triethylorthoformate (0.083 mL, 0.5 mmol) and triethyl amine (0.167 mL, 1.2 mmol) were then added. The reaction was allowed to stand at room temperature for 2 days, poured into diethyl ether (50 mL) and then filtered. The residue was washed with diethyl ether and then dried to yield 0.258 g of 5 as a dark blue solid; $\lambda_{max}$=701 nm(acetone).

Example 7

This example describes the preparation of dye 6:

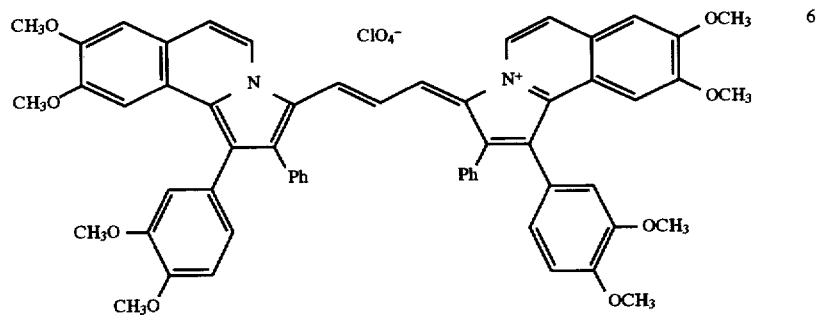

A mixture of 2 (0.439 g, 1 mmol), acetic anhydride (10 mL) and perchloric acid (70%, 0.143 g, 1 mmol) was stirred at room temperature for 5 min. Malonaldehyde bis(dimethyl acetal) (0.083 mL, 0.5 mmol) and triethyl amine (0.167 mL, 1.2 mmol) were then added. The reaction was allowed to stand at room temperature for 3 days, poured into diethyl ether (50 mL) and then filtered. The residue was washed with diethyl ether and then dried to yield 0.150 g of 6 as a dark blue solid; $\lambda_{max}$=750 nm(acetone).

Example 8

This example describes the preparation of dye 7:

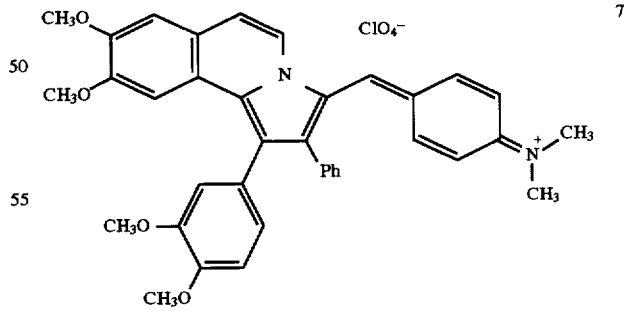

A mixture of 2 (0.329 g, 0.75 mmol), acetic anhydride (5 mL), p-N,N-dimethylaminobenzaldehyde (0.112 g, 0.75 mmol) and perchloric acid (70%, 0.108 g, 0.75 mmol) was allowed to stand at room temperature for 1 day. The reaction mixture was poured into diethyl ether (30 mL) and then filtered. The residue was washed with diethyl ether and dried to yield 0.463 g of 7 as a dark purple solid; $\lambda_{max}$=640 nm(acetone).

Example 9

This example describes the preparation of dye 8:

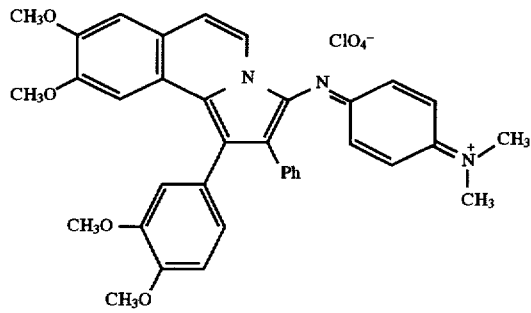

A mixture of 2 (0.329 g, 0.75 mmol), ethanol (5 mL), N,N-dimethyl-p-nitrosoaniline (0.113 g, 0.75 mmol) and perchloric acid (70%, 0.108 g, 0.75 mmol) was heated at reflux for 24 h. The reaction mixture was allowed to cool to room temperature and then diethyl ether (10 mL) was added. The mixture was filtered. The residue was stirred with diethyl ether (30 mL) for 1 h and then the mixture was filtered. The residue was dried to yield 0.338 g of 8 as a brown solid; $\lambda_{max}$=714 nm(acetone).

Example 10

This example describes the preparation of dye 9:

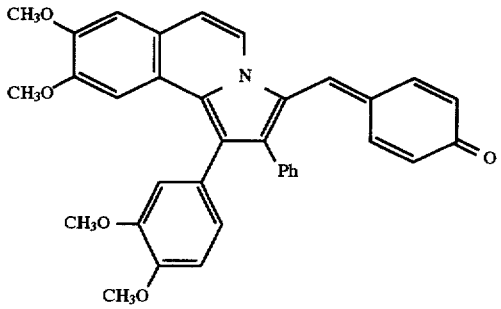

A mixture of 2 (0.220 g, 0.5 mmol), ethanol (10 mL), p-hydroxybenzaldehyde (0.061 g, 0.5 mmol) and perchloric acid (70%, 0.078 g, 0.75 mmol) was allowed to stand at room temperature for 20 h and then filtered. The residue was stirred with ethyl acetate (5 mL) and then filtered. The residue was washed with diethyl ether and then dried to give 0.295 g of 9 as a dark red crystalline solid; $\lambda_{max}$=504 nm(acetone).

Example 11

This example describes the preparation of the intermediate 6,7-dimethoxy-1-[(3,4-dimethoxy)benzyl]-N-acetonylisoquinolinium iodide, 10:

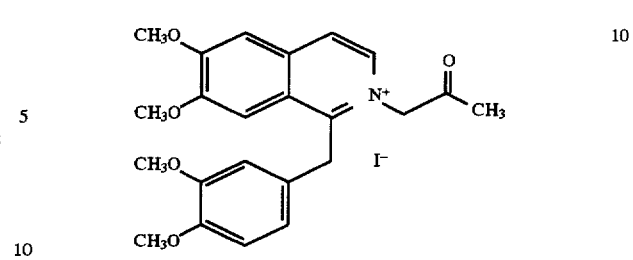

A mixture of sodium iodide (2.99 g, 20 mmol), acetone (20 mL) and chloroacetone (1.31 mL, 16.5 mmol) was allowed to stir for 5 min and then filtered. Papaverine (5.08 g, 15 mmol) was added to the filtrate. The mixture was heated at reflux for 1 h, allowed to cool to room temperature, and then poured into diethyl ether (200 mL). The mixture was filtered and the residue was dried to yield 5.81 g of 10 as a pale yellow solid. $^1$H NMR (400 Mz; d$_6$-DMSO): δ2.29 (s, 3H); 3.68 (s, 6H); 3.94 (s, 3H); 4.08 (s, 3H); 4.88 (s, 2H); 5.92 (s, 2H); 6.52 (d, 1H, J=8.6 Hz); 6.83 (d, 1H, J=8.6 Hz); 7.00 (s, 1H); 7.76 (s, 1H); 7.83 (s, 1H); 8.26 (d, 1H, J=6.8 Hz); 8.35 (d, 1H, J=6.8 Hz).

Example 12

This example describes the preparation of the intermediate 8,9-dimethoxy-1-(3,4-dimethoxy)phenyl-2-methylpyrrolo[2,1-a]isoquinoline, 11:

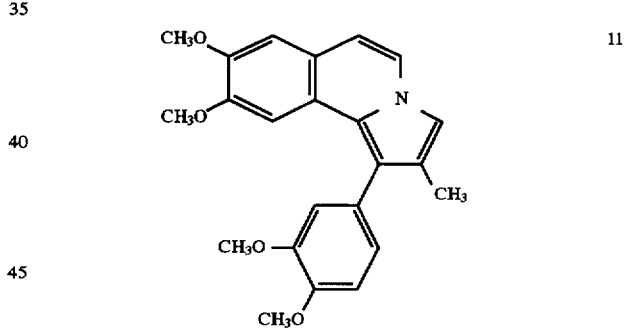

A mixture of 10 (5.51 g, 10.5 mmol), water (350 mL) and sodium bicarbonate (0.885 g) was heated at reflux for 2 h. The reaction mixture was allowed to cool to room temperature and then extracted three times with diethyl ether/ethyl acetate 75:25 (100 mL each). The organic extracts were combined and washed with brine (100 mL), dried using anhydrous magnesium sulfate, filtered and then concentrated to give a tan solid. The solid was recrystallized from ethanol to yield 2.65 g of 11 as a tan solid; m.p. 177°–179° C.; $^1$H NMR (500 Mz; CDCl$_3$): δ2.16 (s, 3H); 3.47 (s, 3H); 3.85 (s, 3H); 3.91 (s, 3H); 3.94 (s, 3H); 6.56 (d, 1H, J=7.2 Hz); 6.90 (s, 1H); 6.98–7.02 (m, 3H); 7.08–7.11 (m, 2H); 7.60 (d, 1H, J=7.2 Hz); $^{13}$C NMR (125 Mz; CDCl$_3$): d 10.66, 55.14, 55.63, 55.71, 55.83, 104.10, 107.56, 109.32, 111.06, 111.85, 114.15, 116.32, 120.45, 121.45, 122.28, 122.65, 123.31, 125.11, 129.67, 147.35, 147.63, 148.32, 148.69.

Example 13

This example describes the preparation of dye 12:

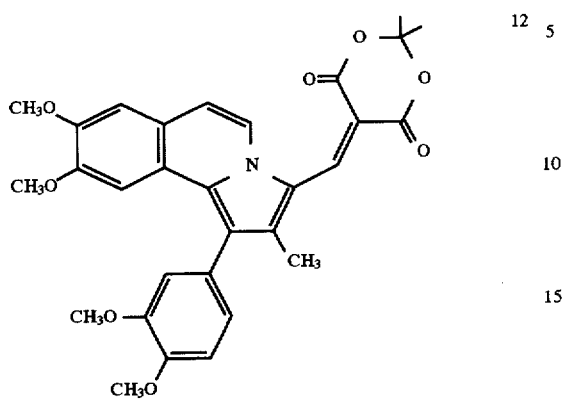

A mixture of 11 (0.377 g, 1 mmol), ethanol (5 mL) and 5-methoxymethylene-1,3-dioxan-4,6-dione (0.195 g, 1.05 mmol) was heated at reflux for 15 min. The reaction mixture was concentrated and the residue recrystallized from ethanol to yield 0.220 g of 12 as an orange-red solid; m.p. 242°–244° C.; $\lambda_{max}$=505 nm(acetone).

Example 14

This example describes the preparation of dye 13:

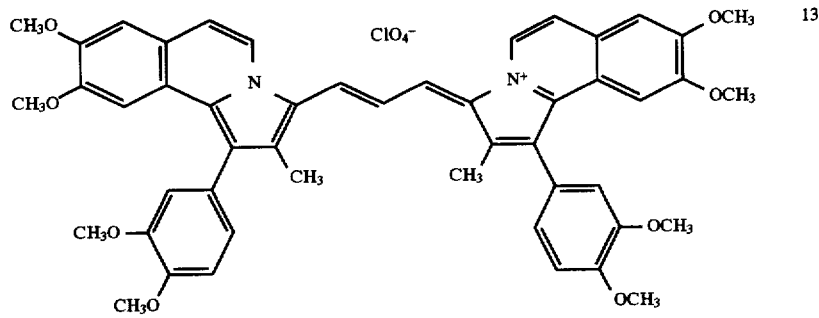

A mixture of 11 (0.377 g, 1 mmol), acetic anhydride (10 mL) and perchloric acid (70%, 0.143 g, 1 mmol) was stirred at room temperature for 5 min. Malonaldehyde bis(dimethyl acetal) (0.083 mL, 0.5 mmol) and triethyl amine (0.167 mL, 1.2 mmol) were then added. The reaction was allowed to stand at room temperature for 1 day and then filtered. The residue was washed with diethyl ether and then dried to yield 0.091 g of 13 as a green solid; $\lambda_{max}$=738 nm(acetone).

Example 15

This example describes the preparation of dye 14:

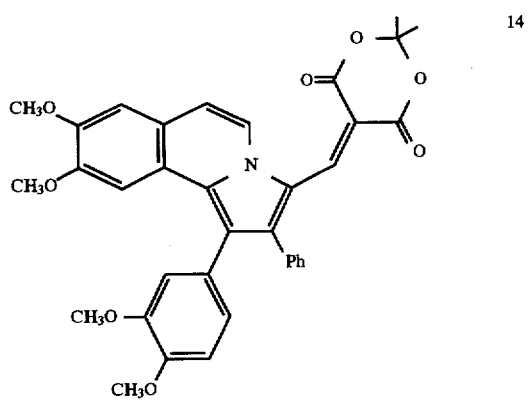

A mixture of 2 (0.439 g, 1 mmol), ethanol (10 mL) and 5-methoxymethylene-1,3-dioxan-4,6-dione (0.195 g, 1.05 mmol) was heated at reflux for 15 min. The reaction mixture was concentrated and the residue recrystallized from a mixture of ethanol and chloroform to yield 0.391 g of 14 as a red-orange solid; m.p. 254°–256° C.; $\lambda_{max}$=511 nm(acetone).

Example 16

This example describes the preparation of the intermediate 8,9-dimethoxy-1-(3,4-dimethoxy)phenyl-2-phenylpyrrolo[2,1-a]isoquinoline-3-carboxaldehyde, 15:

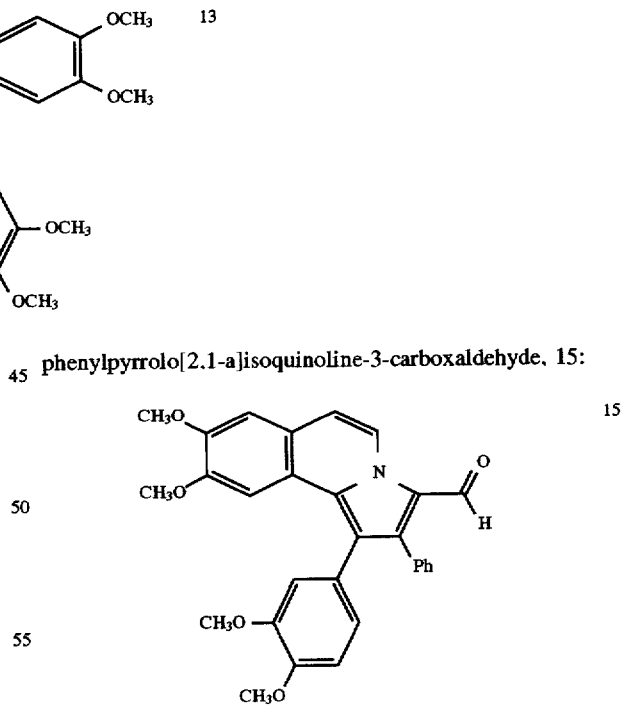

Phosphorus oxychloride (0.103 mL, 1.1 mmol) was added to dimethylformamide (0.50 mL) that was pre-cooled to 5° C. The resulting solution was maintained at 5° C. for 30 min. A solution of 2 (439 mg, 1.0 mmol) in dimethylformamide (3 mL) and dichloromethane (6 mL) was added dropwise over 30 min. The resulting solution was maintained at room temperature for 2 h. The reaction mixture was poured into crushed ice, and then 10% sodium hydroxide (10 mL) was added. The reaction mixture was concentrated to remove the volatile organic solvent. The aqueous mixture was heated at reflux for 15 min. After cooling the mixture to room temperature, it was extracted with chloroform (2 times; 60 mL). The extracts were combined, washed with water (2 times; 50 mL), brine (50 mL), dried over anhydrous magnesium sulfate and then filtered. The organic solvent was removed to leave a pale green solid. The solid was recrystallized from ethanol to give 291 mg of 15 as a pale yellow solid; mp: 221°–223° C.; $^1$H NMR (500 Mz; CDCl$_3$): δ3.47 (s, 3H); 3.72 (s, 3H); 3.89 (s, 3H); 3.99 (s, 3H); 6.82 (d, 1H, J=1.7 Hz); 6.90–6.95 (m, 2H); 7.08–7.09 (m, 2H); 7.22 (s, 1H); 7.29–7.31 (m, 5H); 9.61 (d, 1H, J=7.3 Hz); 9.63 (s, 1H); $^{13}$C NMR (125 Mz; CDCl$_3$): d 55.26, 55.78, 55.84 (2C), 105.37, 106.98, 111.03, 113.25, 114.66, 118.50, 119.01, 121.16, 123.83, 124.01, 125.31, 127.38, 127.75, 131.07, 132.03, 132.20, 140.48, 148.19, 148.70, 149.03, 150.03, 179.08, 196.42; IR (KBr): 1639, 1629, 1224, 862 cm$^{-1}$.

Example 17

This example describes the preparation of dye 16:

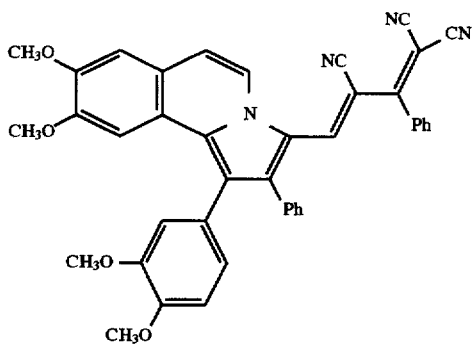

A mixture of 15 (0.234 g, 0.5 mmol), ethanol (15 mL) and 3-dicyanomethylene-3-phenylpropionitrile (0.106 g, 0.55 mmol) was heated at reflux for 15 min. The reaction mixture was concentrated and the residue recrystallized from ethanol to yield 0.142 g of 16 as a dark blue solid; m.p. 145°–147° C.; λ$_{max}$=576 nm(acetone).

Reasonable variations and modifications are possible from the foregoing disclosure without departing from either the spirit or scope of the present invention as recited in the claims.

What is claimed is:

1. A dye having a central pyrrolo[2,1-a]isoquinoline nucleus represented by the formula:

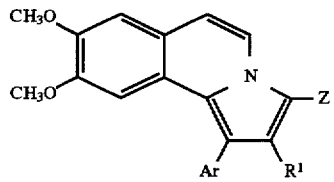

wherein Ar is a phenyl or substituted phenyl group; R$^1$ is an alkyl, alkaryl, aralkyl or aryl group and Z represents the group of atoms that includes either a positively charged nitrogen atom, a carbonyl group, or a nitrile group and completes a conjugate chain between the nitrogen atom of the pyrrolo[2,1-a]isoquinoline nucleus and the positively charged nitrogen atom, the carbonyl group, or the nitrile group contained in Z, conjugate means that the substituent is capable of delocalized bonding between the positively charged nitrogen, carbonyl group or nitrile group within the substituent and the nitrogen of the pyrrolo[2,1-a] isoquinoline nucleus.

2. The dye of claim 1 wherein Z is selected from the group consisting of

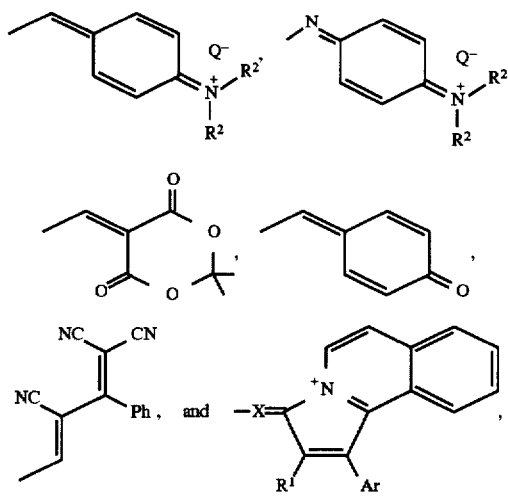

wherein Ar is a phenyl or substituted phenyl group; R$^1$ is an alkyl, alkaryl, aralkyl or aryl group; each R$^2$ is independently an alkyl group having from 1 to 8 carbon atoms; Q$^-$ is an anion; and X is selected from the bridging group consisting of:

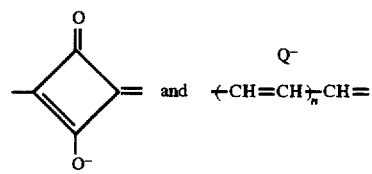

wherein n is 0, 1 or 2 and Q$^-$ is as defined above.

3. The dye of claim 1 wherein Ar is a phenyl group.

4. The dye of claim 1 wherein R$^1$ is a methyl or phenyl group.

5. The dye of claim 2 wherein Q$^-$ is selected from the group consisting of Cl$^-$, Br$^-$, I$^-$, F$^-$, ClO$_4^-$, PF$_6^-$, HSO$_4^-$, HCO$_3^-$, SbF$_6^-$, AsF$_6^-$, R$_f$SO$_3^-$, (R$_f$SO$_2$)$_3$C$^-$, (R$_f$SO$_2$)$_2$HC$^-$, and (R$_f$SO$_2$)$_2$N$^-$ wherein R$_f$ represents a perfluoroalkyl group or two R$_f$ groups taken together represent the necessary atoms to form a five- or six-membered perfluorinated ring.

6. The dye of claim 2 wherein each R$^2$ is a methyl or ethyl group.

7. The dye of claim 2 wherein Q$^-$ is ClO$_4^-$.

8. A dye of the formula:

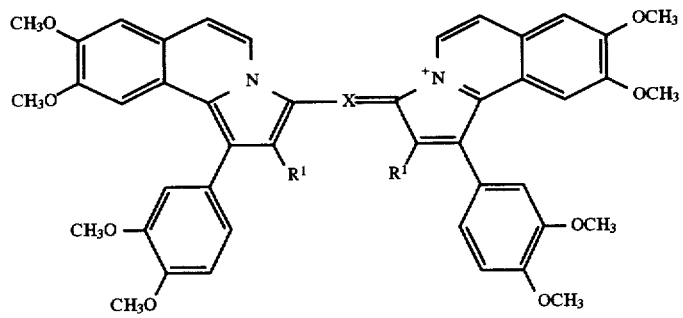

wherein $R^1$ is an alkyl, alkaryl, aralkyl or aryl group and X is selected from the bridging groups consisting of:

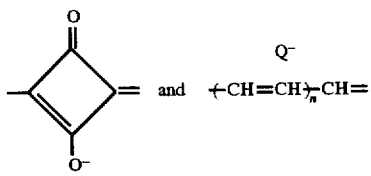

wherein n is 0, 1 or 2 and $Q^-$ is an anion.

9. The dye of claim 8 wherein $R^1$ is a methyl or phenyl group.

10. The dye of claim 8 wherein $Q^-$ is selected from the group consisting of $Cl^-$, $Br^-$, $I^-$, $F^-$, $ClO_4^-$, $PF_6^-$, $HSO_4^-$, $HCO_3^-$, $SbF_6^-$, $AsF_6^-$, $R_fSO_3^-$, $(R_fSO_2)_3C^-$, $(R_fSO_2)_2HC^-$, and $(R_fSO_2)_2N^-$ wherein $R_f$ represents a perfluoroalkyl group or two $R_f$ groups taken together represent the necessary atoms to form a five- or six-membered perfluorinated ring.

11. The dye of claim 8 wherein $Q^-$ is $ClO_4^-$.

12. A dye of the formula:

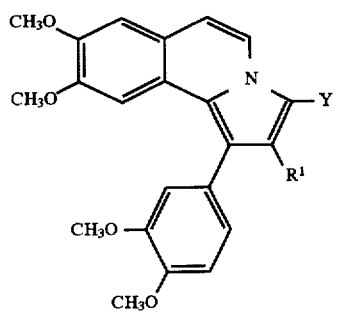

wherein $R^1$ is an alkyl, alkaryl, aralkyl or aryl group and Y is selected from the group consisting of:

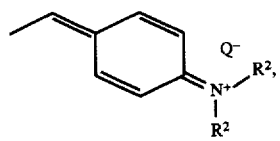

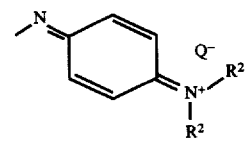

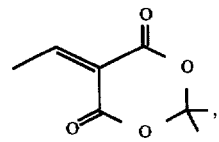

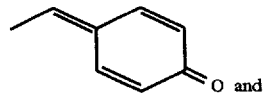

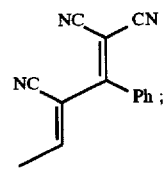

wherein each $R^2$ is independently an alkyl group having from 1 to 8 carbon atoms and $Q^-$ is an anion.

13. The dye of claim 12 wherein $R^1$ is a methyl or phenyl group.

14. The dye of claim 12 wherein each $R^2$ is a methyl or ethyl group.

15. The dye of claim 12 wherein $Q^-$ is selected from the group consisting of $Cl^-$, $Br^-$, $I^-$, $F^-$, $ClO_4^-$, $PF_6^-$, $HSO_4^-$, $HCO_3^-$, $SbF_6^-$, $AsF_6^-$, $R_fSO_3^-$, $(R_fSO_2)_3C^-$, $(R_fSO_2)_2HC^-$, and $(R_fSO_2)_2N^-$ wherein $R_f$ represents a perfluoroalkyl group or two $R_f$ groups taken together represent the necessary atoms to form a five- or six-membered perfluorinated ring.

16. The dye of claim 12 wherein $Q^-$ is $ClO_4^-$.

* * * * *